United States Patent
Bacik (10) Patent No.: US 12,036,143 B2
(45) Date of Patent: Jul. 16, 2024

(54) SPLINT

(71) Applicant: Tala, LLC, Scottsdale, AZ (US)

(72) Inventor: John Andrew Bacik, Scottsdale, AZ (US)

(73) Assignee: Tala, LLC, Scottsdale, AZ (US)

( * ) Notice: Subject to any disclaimer, the term of this patent is extended or adjusted under 35 U.S.C. 154(b) by 396 days.

(21) Appl. No.: 17/382,641

(22) Filed: Jul. 22, 2021

(65) Prior Publication Data

US 2022/0039992 A1 Feb. 10, 2022

Related U.S. Application Data

(60) Provisional application No. 63/103,448, filed on Aug. 7, 2020, provisional application No. 63/103,999, filed on Sep. 8, 2020.

(51) Int. Cl.
*A61F 5/058* (2006.01)

(52) U.S. Cl.
CPC .................. *A61F 5/05875* (2013.01)

(58) Field of Classification Search
CPC .. A61F 5/00; A61F 5/01; A61F 5/0118; A61F 5/013; A61F 5/04; A61F 5/042; A61F 5/058; A61F 5/05841; A61F 5/0585; A61F 5/05866; A61F 5/05875; A61F 5/10;
(Continued)

(56) References Cited

U.S. PATENT DOCUMENTS 5,947,915 A 9/1999 Thibodo, Jr.
6,575,925 B1 6/2003 Noble
(Continued)

FOREIGN PATENT DOCUMENTS

KR 10-0963469 B1 6/2010
KR 963469 B1 * 6/2010

OTHER PUBLICATIONS

Machine translation of Publication No. KR 100963469 created Oct. 12, 2023 from Espacenet [retrieved from https://worldwide.espacenet.com/patent/search/family/040992760/publication/KR100963469B1?q=KR%20100963469] (Year: 2010).*

(Continued)

*Primary Examiner* — Ophelia A Hawthorne
*Assistant Examiner* — Gina McCarthy
(74) *Attorney, Agent, or Firm* — Whitley Legal Group, PC; Annmarie W Whitley (57) ABSTRACT

An improved finger splint includes an outer frame that partly surrounds an inner comfort sleeve. The outer frame is a substantially tubular shape with an oblong opening that cooperates with a patient's knuckle when the patient wears the splint around his finger and a pair of spine areas that extend along the underside of the patient's finger to encourage extension. The inner comfort sleeve includes a channel on its outer surface for receiving the outer frame, ridges along its inner surface, and holes and slots extending between its outer and inner surfaces to facilitate adjustment and breathability. Optionally, a fingertip guard can be removable attached to the inner sleeve with a series of protrusions that cooperate with the holes positioned around the inner sleeve. When assembled, the outer frame and inner comfort sleeve create a low profile, comfortable, and attractive and customizable splint.

20 Claims, 6 Drawing Sheets

(58) Field of Classification Search
CPC ............... A61F 5/11; A41D 19/01517; A41D 19/01582; A41D 19/01588; A41D 13/087
See application file for complete search history.

(56) References Cited

U.S. PATENT DOCUMENTS

| | | | |
|---|---|---|---|
| 2003/0135143 A1* | 7/2003 | Chow ................ | A61F 5/05875 602/22 |
| 2006/0276735 A1 | 12/2006 | Phelan et al. | |
| 2010/0262057 A1 | 10/2010 | Chandrasekar et al. | |
| 2014/0188237 A1* | 7/2014 | McCormick ........ | A61F 5/05875 623/21.19 |

OTHER PUBLICATIONS

International Search Report and Written Opinion of the International Search Authority for PCT/US2021/049248 dated Dec. 23, 2021, Korean Intellectual Property Office.

\* cited by examiner

SPLINT

CROSS-REFERENCE TO RELATED APPLICATIONS

This application claims the benefit of provisional U.S. Application 63/103,448 filed Aug. 7, 2020 and U.S. Provisional Application 63/103,999 filed Sep. 8, 2020.

FIELD OF INVENTION

This invention relates to splints, braces, and immobilizers. More particularly, this invention relates to an improved finger splint.

BACKGROUND

Splints, braces, and immobilizers can be used to improve physical function, slow disease progression, and diminish pain. For example, knee braces are recommended for patients suffering from osteoarthritis, and knee immobilizers might be used for acute traumatic injuries. For acute ankle sprains, functional ankle braces provide support without immobilization, and semirigid ankle braces decrease the risk of future ankle sprains in patients with a history of ankle sprain. For chronic injuries such as carpal tunnel syndrome, a neutral wrist sprint can be used. Whether to immobilize an unstable joint or fracture, to reduce the load carried by a joint, to improve pain and function, or to eliminate or modify range of motion, splints and braces provide a low cost and patient accepted method of treating or managing musculoskeletal disorders with few adverse effects.

Many finger injuries are treated with splinting or bracing. For example, two common finger injuries experienced by athletes requiring intervention are the boutonniere finger injury and the mallet finger injury. Boutonniere deformities are caused when a tendon tears over the middle finger joint and the supporting ligament is also injured. As a result, the athlete cannot fully straighten the middle joint of the finger. Treated early with a splint that completely straightens the middle joint but allows for the tip of the finger to be frequently exercised, the issue resolves after six weeks with little or no formal hand therapy. Likewise, Mallet finger injuries occur when the athlete's terminal tendon tears, sometimes accompanied by a fracture, and look as if the tip of the athlete's finger has dropped. To treat the Mallet finger, the tip joint of the finger is splinted in full extension to correct the deformity and prevent instability. As with Boutonniere deformities, Mallet finger resolves after several weeks of splinting with little or no formal hand therapy.

In addition to athletic or acute finger injures, a variety of finger splints and braces can be used to reduce pain and treat other injuries and chronic conditions. For example, thumb splints can be used to treat joint injuries known as skier's or gatekeeper's thumb, drift hand splints can be used to treat arthritis and provide knuckle support, multi-finger extension braces can be used to treat Dupuytren's Contracture and metacarpal fracture, immobilizer splints can be used to combat trigger finger, and swan or boutonniere ring splints can be used to support finger joints plagued by osteoarthritis or rheumatoid arthritis.

While treating joint or finger injuries and deformities with a splint that fully or partly immobilizes the finger joints in extension is common, currently available splints and braces are bulky, inconvenient, and often unsightly for patients to wear as they go about their day. Additionally, they often lack breathability, can require frequent adjustment due to increasing or decreasing swelling, and must be removed or protected each time a patient washes his hands. Because of this, patients might remove their splint when away from home, which negatively impacts the speed of their recovery. Accordingly, it would be desirable to provide a low profile finger splint. It would be further desirable to provide a finger splint that reduces the need for frequent adjustments, is breathable, can be washed while in use, and provides additional features to aid with healing.

SUMMARY OF THE INVENTION

An improved splint for fingers includes an outer rigid or semirigid frame that partly surrounds an inner comfort sleeve. The outer frame is made of a plastic, metal, or rubber, or other material that can be molded or formed into a substantially tubular shape and preferably defines an oblong opening that cooperates with a patient's knuckle when the patient wears the splint around his finger or thumb. The outer frame also encircles the patient's finger such that two rigid spine areas of the frame are positioned at least partly on the underside of the patient's finger to resist flexion and encourage extension. The inner comfort sleeve can be a closed tubular sleeve with a fixed diameter that preferably tapers from a larger proximal end to a smaller distal end, an open sleeve with an adjustable diameter, or a modified closed sleeve with a somewhat adjustable diameter. The inner sleeve has an outer surface with channels that cooperate with and accept the outer frame. It also has an inner surface that preferably includes a plurality of longitudinal ridges to promote breathability and allow water drainage. Extending through the body of the inner sleeve, there also are several holes positioned to further increase airflow, to increase flexibility and adjustability, and to facilitate connection with an optional guard attachment that removably attaches to the distal end of the inner sleeve to extend around and protect the tip of a patient's finger or thumb. Additionally, the inner comfort sleeve can include an inner lining that provides constant cooling or can be refrigerated prior to use for temporary cooling. When assembled, the outer frame and inner comfort sleeve create a low profile, comfortable, and attractive splint that can be customized with logos and by using materials in a variety of colors and patterns.

DETAILED DESCRIPTION OF THE INVENTION

Figure 7A:
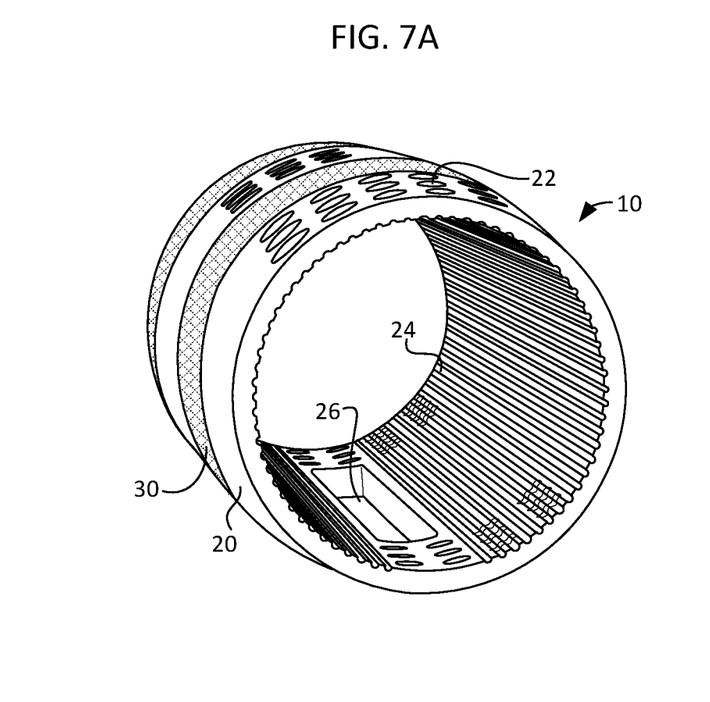
FIG. 7A is an end perspective view of the splint the present invention with the second embodiment of the inner comfort sleeve.
Figure 7B:
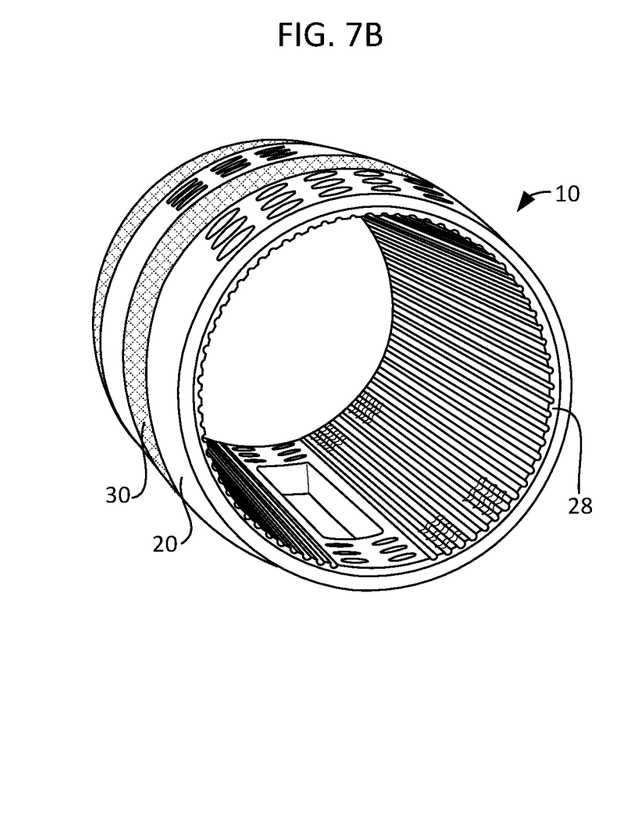
FIG. 7B is an end perspective view of the splint the present invention with a third embodiment of the inner comfort sleeve.
Figure 8:
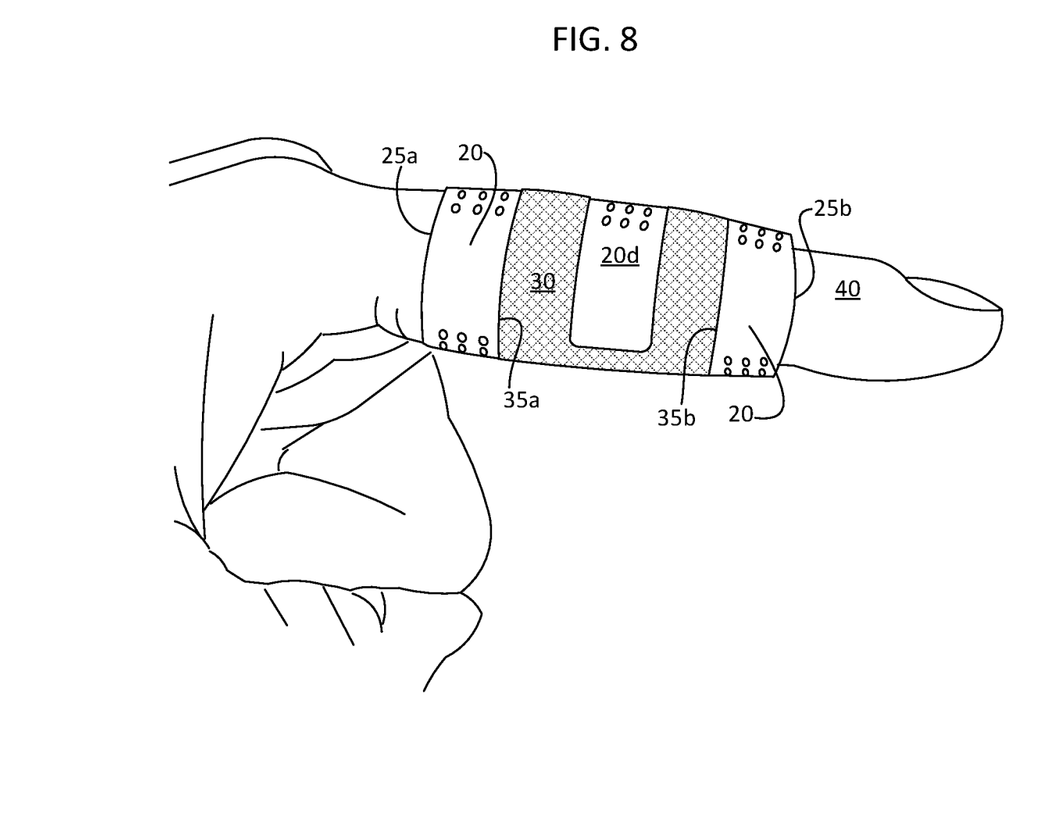
FIG. 8 is an illustration of the splint of the present invention positioned on a patient's finger.

An improved splint 10 for fingers includes an outer rigid or semirigid frame 30 that partly surrounds an inner comfort sleeve 20 is shown in FIGS. 1-9. Outer frame 30 provides a rigid structure for securing a patient's finger 40 or thumb in extension, and inner comfort sleeve 20 provides a barrier between outer frame 30 and the patient's finger 40 to increase airflow, adjustability, optional compression, and overall comfort. When assembled, outer frame 30 and inner comfort sleeve 20 create a low profile, comfortable, and attractive splint, as shown in FIG. 8, that can be customized with logos and by using materials in a variety of colors and patterns. While a splint for a finger is discussed and shown in the Figures, it is anticipated that the design shown can be scaled up or down for use on other joints where extension is desired such as toes, wrists, arms, elbows, knees, and legs.

Figure 1:
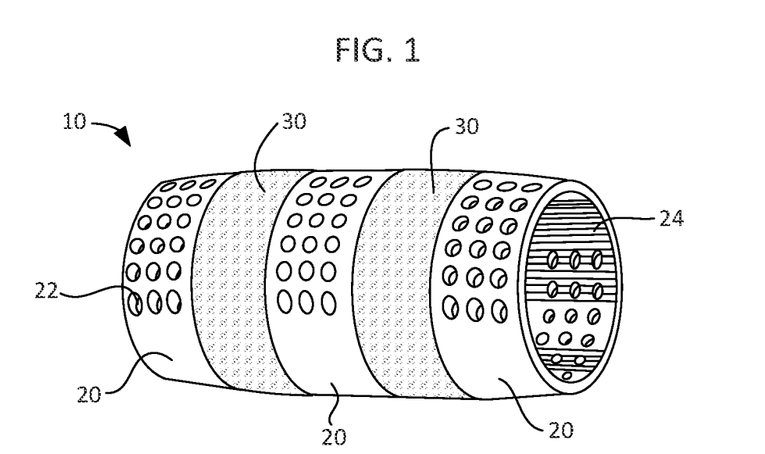
FIG. 1 is a perspective view of the splint of the present invention.
Figure 2:
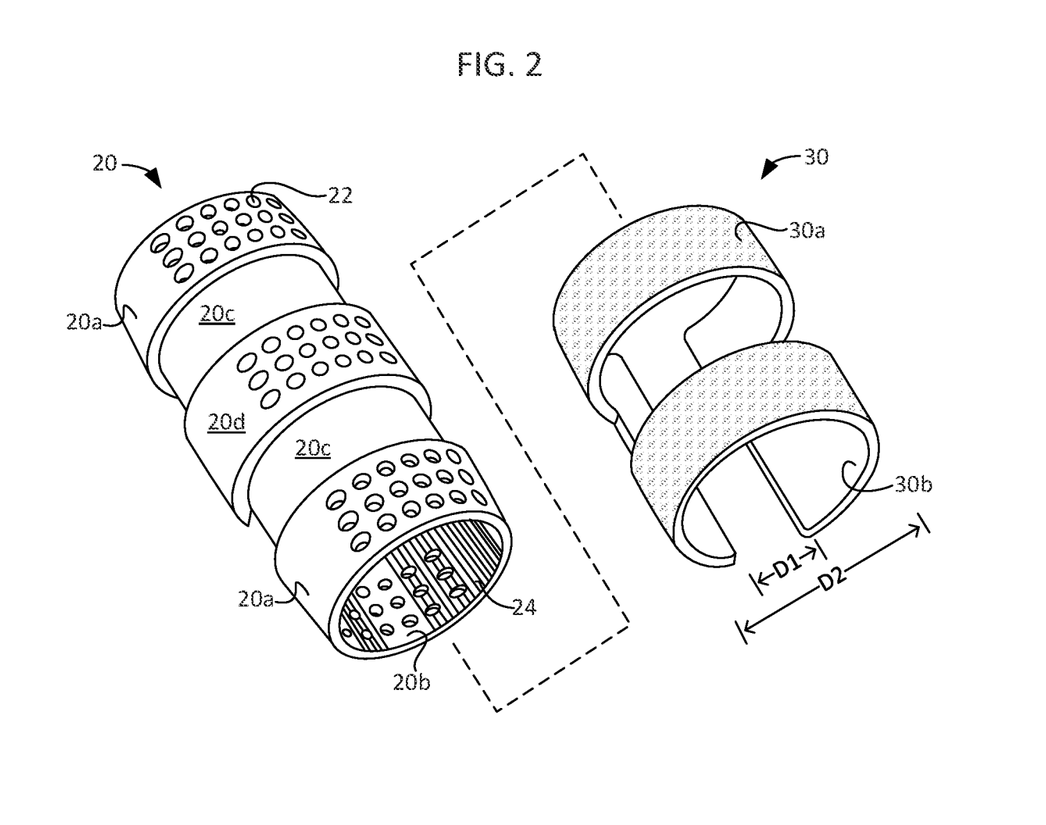
FIG. 2 is an exploded view of the splint of the present invention.
Figure 5:
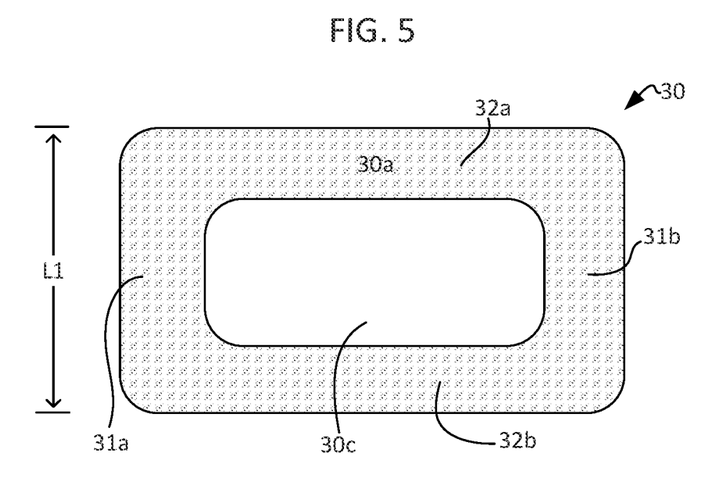
FIG. 5 is a top view of the flattened shape of the outer frame of the splint of the present invention.
Figure 6:
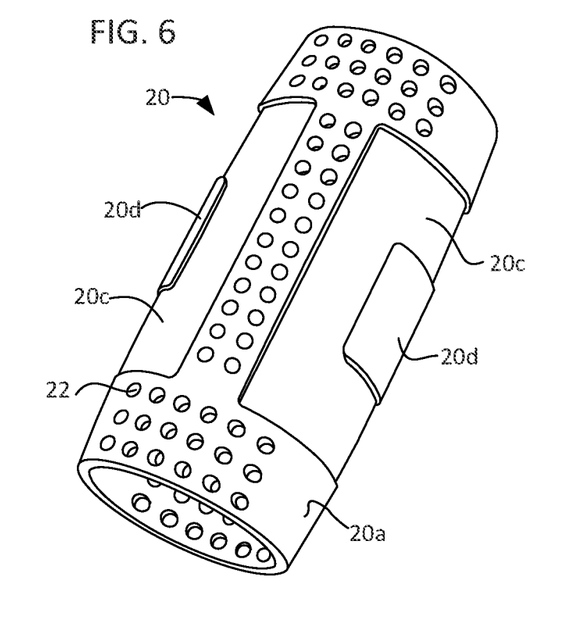
FIG. 6 is a perspective view of the first embodiment of the inner comfort sleeve of the splint of the present invention.

As shown in FIGS. 2 and 5, in particular, outer frame 30 has an outer surface 30*a* and an inner surface 30*b*. Further, outer frame 30 defines a frame opening 30*c* that is surrounded by integrally connected first and second spine sections 31*a* and 31*b* of outer frame 30 and first and second ring sections 32*a* and 32*b* of outer frame 30. FIG. 5 shows the overall shape of outer frame 30 if it were flattened rather than formed into an open tube. When in use, outer frame 30 encircles the patient's finger such that two rigid spine areas 31 of the frame are positioned at least partly on the underside of the patient's finger to resist flexion and encourage extension, and the ring sections 31 extend around the patient's finger on either side of the splinted joint. Opening 30*c* is sized such that when positioned over a patient's finger, opening 30*c* accommodates the patient's knuckle. Accordingly, the patient does not face resistance from a rigid or semirigid material at his knuckle. Opening 30*c* is illustrated as a rounded oblong substantially rectangular shape, which is preferred. Alternatively, opening 30*c* can be any shape that accommodates a patient's knuckle, such as irregular, oval, or round.

As shown in FIG. 5, the overall length L1 of outer frame 30 corresponds in part to the length of a patient's finger. Preferably, L1 is around 37 mm or between 27 mm and 47 mm, but it can be any length that fits on a patient's finger and larger or smaller depending on whether it will be used toward the tip of a patient's finger or over the middle finger joint. The size of ring sections 32 and spine sections 31 can be large or small and will decrease in size as opening 30*c* increases in size. Additionally, while ring sections 32 are illustrated as two ring sections of equal size and shape, they can vary in size and shape. Additionally, while spine sections 31 are illustrated as two spine sections of equal size and shape, they can vary in size and shape. For example, opening 30*c* could be irregular in shape or an oval shape centered or not centered on the overall frame, which would change the size and shapes of ring sections 32 and spine sections 31. Additionally, the overall geometry can reflect a slight taper when formed in an open tube. Preferably, the taper is between 2 degrees and 4 degrees.

FIG. 2 illustrates outer frame 30 when formed as intended into an open tube where its two spines sit adjacent one another at a spaced distance D1. Spaced distance D1 is preferably around 16 mm at its largest point or between 7 mm and 22.5 mm, but it can be any distance as long as spines 31 provide resistance to flexion of the finger. Alternatively, spaced distance D1 can be nonexistent or negligible, and sides 31 can be adjoining. The overall inner diameter of outer frame 30 is shown as D2 in FIG. 2. Preferably diameter D2 is slightly larger than the diameter of a patient's finger and large enough to accommodate inner comfort sleeve 20. For example, if a patient's finger is 17 mm, then diameter D2 would be 19 mm, which would be about the same as the typical ring size 9 or 10. More preferably, diameter D2 decreases in size slightly from it proximal end 35*a* to its distal end 35*b* as shown in FIG. 8. Preferably, the taper is about or between 2 degrees and 4 degrees.

Outer frame 30 is preferably made of a plastic, metal, or rubber, or other material that can be molded or formed into a substantially open tubular shape and is of a thickness sufficient to provide adequate resistance to flexion of the targeted joint. Outer frame 30 is preferably made from a material that is semirigid and resilient. Preferably, outer frame 30 is made from thermoplastic and amorphous polymer such as acrylonitrile butadiene styrene (ABS). Outer frame 30 can be removably attachable to cooperating inner sleeve 20 but preferably it is fixedly attached. For example, outer frame 30 can be attached to inner sleeve 20 using over-molding or other multi-material molding processes.

Figures 3, 4:
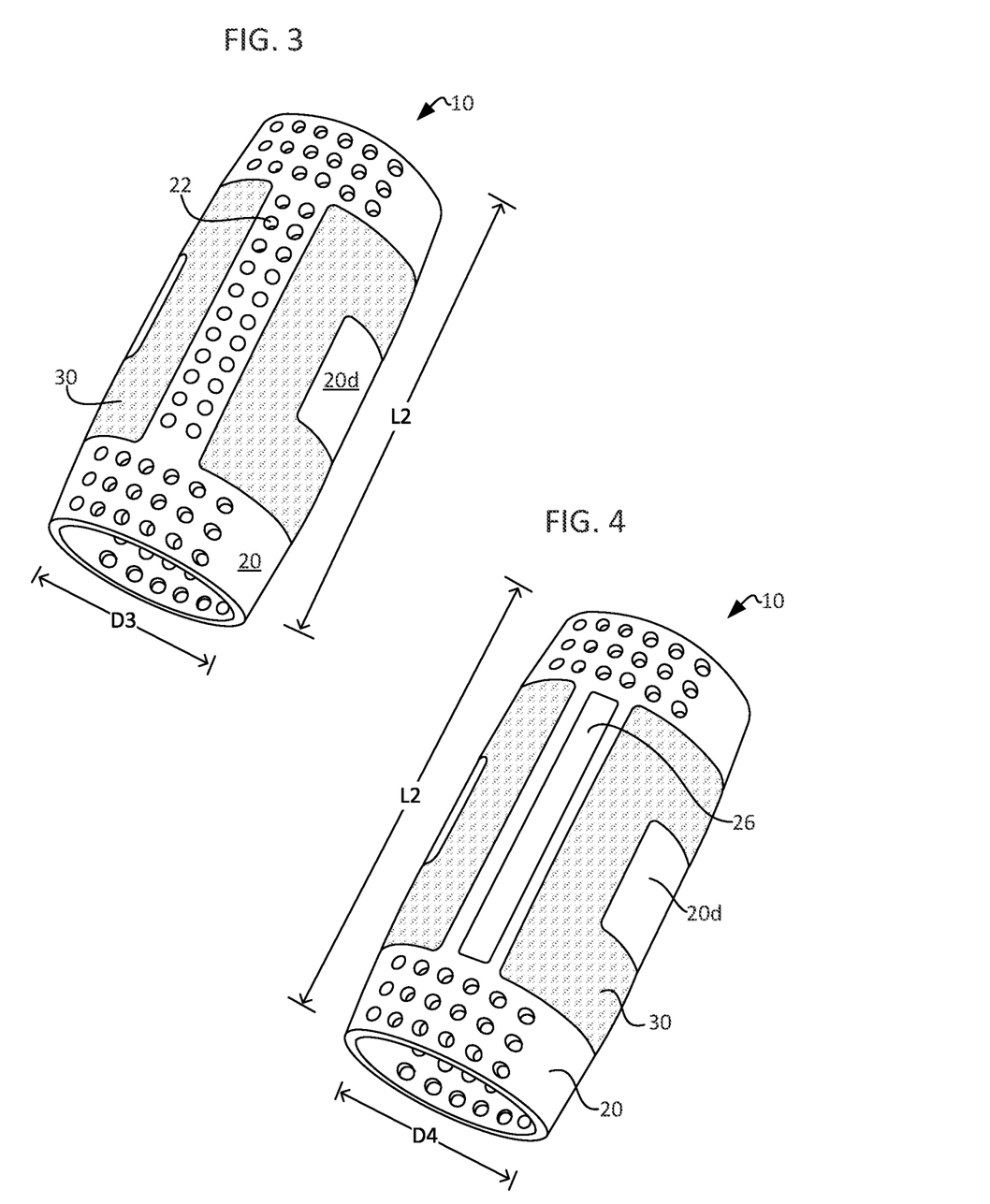
FIG. 3 is a perspective view of the present invention with a first embodiment of the inner comfort sleeve.
FIG. 4 is a perspective view of the present invention with a second embodiment of the inner comfort sleeve.

FIGS. 2-4 and 6-7B illustrate several embodiments of a flexible inner comfort sleeve 20. Generally, inner sleeve 20 can be a closed tubular sleeve with a substantially fixed diameter that preferable tapers from a larger fixed diameter at its proximal end to a smaller fixed diameter at its distal end, an open sleeve with an adjustable diameter, or a modified closed sleeve with a somewhat adjustable diameter. Preferably, inner sleeve 20 is a closed tubular sleeve with a substantially fixed inner diameter D3 as shown in FIG. 3 or a modified closed sleeve with a somewhat adjustable inner diameter D4 as shown in FIG. 4, both of which will be described below. Additionally, while described has having a fixed or somewhat adjustable diameter D3 or D4, it is anticipated that the diameter of inner sleeve 20 in each embodiment will adjust somewhat when in use as it conforms to the patient's finger shape and size. Preferably, the diameter of inner sleeve tapers at about or between 2 degrees and 4 degrees from its larger proximal end to its smaller distal end as shown in FIG. 8.

Inner comfort sleeve 20 is preferably comprised of a flexible and resilient material that is also preferably waterproof. Optionally, it can be made of a flexible material with compression properties or it may be made of a cooling material, a material that offers heat. Alternatively, it can be made of a combination of such materials such as a flexible core material with a cooling lining. Preferably, sleeve 20 is made from thermoset rubbers including ethylene propylene diene monomer (EPDM), thermoplastic vulcanizates (TPVs), or a thermoplastic elastomer (TPE) such as chemically bonded Santoprene from Exxon Mobile of Irving, Texas Inner sleeve 20 is preferably about 1 mm thick or between 0.5 mm and 1.5 mm thick with a diameter that is substantially equal to or slightly larger than the diameter of a patient's finger.

As shown in FIGS. 3 and 4, the overall length L2 of inner sleeve 20 corresponds in part to the length of a patient's finger. Preferably, L2 is about 55 mm or a length between 45 mm and 65 mm, but it can be any length that fits on a patient's finger and can be larger or smaller depending on whether it will be used toward the tip of a patient's finger or over the middle finger joint. Length L2 is larger than length L1 as shown in the Figures.

As shown in FIG. 2, inner sleeve 20 has an outer sleeve surface 20a that defines a recessed channel 20c on its outer surface. Channel 20c is sized and shaped to receive outer frame 30 and is continuous such that it surrounds a flex region 20d of sleeve 20. The 20d cooperates with opening 30c of frame 30 and fits over the knuckle regions of the patient's joint that is targeted by the splint, as shown in FIG. 8. Preferably, the depth of channel 20c corresponds to the thickness of outer frame 30 so that when outer frame 30 is positioned in channel 20c the outer frame surface 30a of outer frame 30 is flush with or only slightly raised from the outer sleeve surface 20a of inner comfort sleeve 20. Alternatively, channel 20c can be shallower or deeper than the thickness of outer frame 30 as long as it securely holds outer frame 30 in place around inner comfort sleeve 20.

Inner sleeve 20 also has an inner sleeve surface 20b, which can be smooth or have ridges, nodules, or other protrusions or features. Preferably, inner sleeve surface 20b includes several longitudinal ridges 24 extending from one end of the inner sleeve 20 to the opposite end of inner sleeve 20. Ridges 24 can be evenly spaced around the inner sleeve surface 20b or placed in groups or irregularly spaced. Ridges 24 assist with placement of the sleeve over the finger and promote breathability. Additionally, they allow sweat and water to drain away from the splinted finger. FIGS. 7A and 7B illustrate an embodiment where ridges 24 are spaced uniformly around a substantial portion of inner sleeve surface 20b.

Additionally one or more openings, vents, or holes 22 can be defined by inner sleeve 20 where the holes extend from the outer sleeve surface 20a to the inner sleeve surface 20b. FIG. 3 illustrates a plurality of holes 22 positioned around a substantially fixed diameter closed inner comfort sleeve 20. The plurality of holes 22 promote breathability and accommodate expansion and contraction of the sleeve as needed to place it over the finger or to adjust to swelling or various finger sizes. FIG. 4 illustrates the plurality of holes 22 positioned around a modified closed sleeve 20 with a somewhat adjustable diameter. With this embodiment, however, preferably a slot 26 also extends from inner sleeves outer sleeve surface 20a to inner sleeve surface 20b. As shown in FIG. 4, it is further preferably positioned to extend longitudinally between and parallel to section of channel 20c that accommodates the spine areas 31 of outer frame 30. The slot allows for more variability of the inner diameter of inner sleeve 30 such that it is a modified closed design. To convert the modified closed design to an open sleeve design, the patient can extend slot 26 by cutting at each of its ends. Alternatively, a slot can extend longitudinally from one end to the other of inner sleeve 20 to create an open sleeve design.

In an alternative embodiment, as shown in FIG. 7B, inner comfort sleeve 20 can include an inner lining 28 or encasement that facilitates healing or further comfort. For example, inner lining might be a cooling gel adhered to the inner surface 20b of sleeve 20, where the cooling gel either continuously cools the patient's finger when in use or can be frozen before use for temporary relief. Alternatively, it might be a warming material that offers heat to increase comfort or a soft material that prevents irritation and wicks moisture.

FIGS. 9-12 illustrate an optional fingertip guard 50 that can be removably attached to inner sleeve 20. Guard 50 includes a distal tip end 52 that has an inner surface 52a, an outer surface 52b, and a recess 52c defined by the inner surface 52a and configured to receive or cradle the tip of a patient's finger 40 or thumb, a proximal guard spine 54 having an inner surface 54a and an outer surface 54b, and an optional transition section 56 having an inner surface 56a and an outer surface 56b. Transition section 56 connects the distal tip end 52 with the proximal guard spine 54. Where no transition section 56 is present, then distal tip end 52 and proximal guard spine 54 connect directly. Preferably, distal tip end 52, transition section 56 when present, and proximal guard spine 54 are integrally formed either from the same material as inner sleeve 20 where a flexible guard is desired or the same material as outer frame 30 where a more rigid guard is desired. Optionally, proximal guard spine 54 and distal tip end 52 can be comprised of differing materials such as, for example, where it is desirable to have a rigid proximal guard spine 54 but a more flexible distal tip end 52. Distal tip end 52 can be any length suitable to cover the tip of a patient's finger while still able to attach to inner sleeve 20 and preferably is about 17 mm long or between 15 and 35 mm long. Guard spine 54 can extend along the entire length of inner sleeve 20 or extend only enough to secure attachment to inner sleeve 20. Preferably guard spine 45 is approximately one half of the length L2 of inner sleeve 20.

Figure 10:
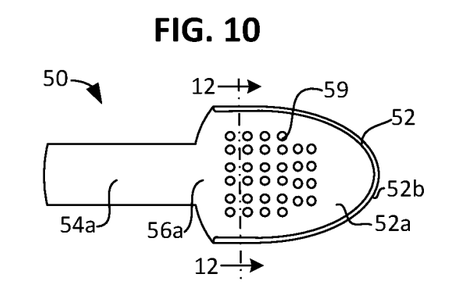
FIG. 10 is a top view of the alternate embodiment of the splint of the present invention.
Figure 11:
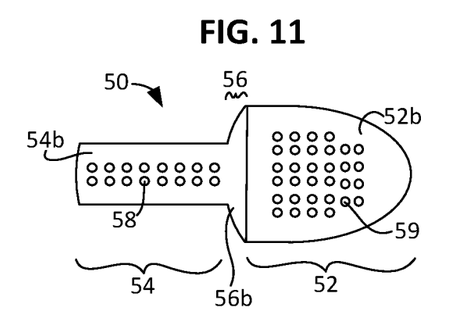
FIG. 11 is a bottom view of the alternate embodiment of the splint of the present invention.
Figure 12:
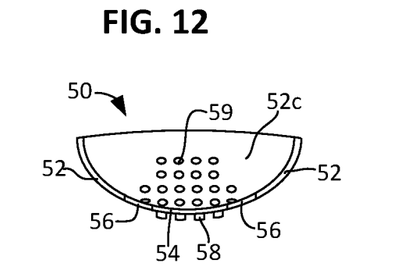
FIG. 12 is view of the embodiment of the splint shown in FIG. 10 cut along the line 12-12.

Preferably, along the outer surface 54b of spine 54 are several protrusions 58 that cooperate with the openings 22 of the inner sleeve 20 to removably attach guard 50 to inner sleeve 20. Guard protrusions 58 are preferably integrally formed with spine 54 such that can easily be inserted in and removed from openings 22 and arranged in a pattern that aligns with the openings 22 to facilitate adjustment of guard 50 relative to the inner sleeve 20. Accordingly, guard 50 can be attached in a variety of positions relative to inner sleeve 20.

Optionally, one or more openings, vents, or holes 59 can be defined by tip end 52 where the holes extend from the tip end outer surface 52a to the tip end inner surface 52b. The plurality of holes 59 promote additional breathability of guard 50. Also optionally, one or more holes (not shown) can extend from the outer surface 56a to the inner surface 56b of the transition section 56 as well. Alternatively, one or more protrusions (not shown) can extend from the outer surface 56b of the transition section as well to further facilitate attachment inner sleeve 20.

Figure 9:
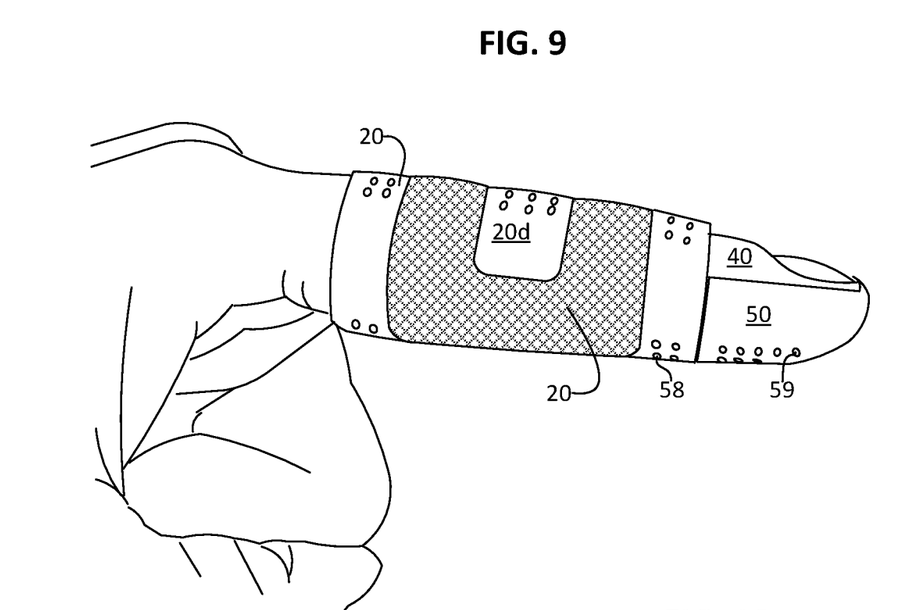
FIG. 9 is an illustration of an alternative embodiment of the splint of the present invention positioned on a patient's finger.

To use splint 10, a patient slides the inner comfort sleeve 20 or the entire splint 10 over his finger and positions it so that channel 20c surrounds the knuckle of the injured or painful joint and such that the guard 50 extends to the tip of the patient's finger if using guard 50. Where the outer frame 30 removably attaches to inner sleeve 20, once inner sleeve 20 is correctly positioned, then outer frame 30 can be pulled open slightly at its spine areas 31, slipped over inner sleeve 20, and positioned around inner sleeve 20 at channel 20c. Likewise, splint 10 can be removed by first removing the frame 30 when appropriate and then sliding off sleeve 20. As FIGS. 8 and 9 show, outer frame 30 provides a rigid structure for securing a patient's finger 40 or thumb in extension while inner comfort sleeve 20 provides a barrier between outer frame 30 and the patient's finger 40 to increase airflow, adjustability, optional compression, and overall comfort and optional guard 50 protects the tip of the patient's finger 40 or thumb. When assembled, outer frame 30 and inner comfort sleeve 20 create a low profile, comfortable, and attractive splint 10. Due to its low profile, splint 10 can be worn under gloves and can be worn more comfortably when engaging in normal daily activities. Splint 10 can be additionally customized with logos and by using materials in a variety of colors and patterns. Moreover, both the outer frame 30 and inner sleeve 20 can be swapped with similarly sized frames 30 and sleeves 20 to accommodate different settings, fashion needs, or institutional affiliations.

While there has been illustrated and described what is at present considered to be the preferred embodiment of the present invention, it will be understood by those skilled in the art that various changes and modifications may be made and equivalents may be substituted for elements thereof without departing from the true scope of the invention disclosed, but that the invention will include all embodiments falling within the scope of the claims.

I claim:

1. A splint comprising:
   a) a flexible tubular inner sleeve having an inner diameter, an outer sleeve surface, and an inner sleeve surface, wherein the outer sleeve surface defines a channel on its outer sleeve surface and wherein the channel surrounds a flex region of the inner sleeve, the flex region being configured to cooperate with a bodily joint; and
   b) a semi-rigid and resilient tubular outer frame having an inner diameter and defining a frame opening, wherein the outer frame is configured to cooperate with the channel of the inner sleeve, the frame opening is configured to cooperate with the flex region of the inner sleeve when the outer frame is positioned in the channel of the inner sleeve, and the outer frame comprises:
      i) a first ring section having a first end and second end;
      ii) a second ring section having a first end and a second end, wherein the second ring section is offset from the first ring section;
      in a first spine section connecting the first end of the first ring section to the first end of the second ring section; and
      iv) a second spine section connecting the second end of the first ring section to the second end of the second ring section, wherein the second spine section is offset from the first spine section and the connected first ring section, first spine section, second ring section, and second spine section define the perimeter of the frame opening of the outer frame.

2. The splint of claim 1 wherein the inner sleeve defines a plurality of holes extending from its outer sleeve surface to its inner sleeve surface.

3. The splint of claim 2 wherein the inner sleeve further defines a slot extending from its outer sleeve surface to its inner sleeve surface.

4. The splint of claim 3 wherein the inner diameter of the tubular inner sleeve tapers from a larger proximal end to a smaller distal end and wherein the inner diameter of the open tubular outer frame tapers from a larger proximal end to a smaller distal end.

5. The splint of claim 4 wherein the degree of taper is equal to or between 2 degrees and 4 degrees.

6. The splint of claim 3 wherein the inner sleeve surface defines a plurality of longitudinal ridges.

7. The splint of claim 2 wherein the inner diameter of the tubular inner sleeve tapers from a larger proximal end to a smaller distal end and wherein the inner diameter of the open tubular outer frame tapers from a larger proximal end to a smaller distal end.

8. The splint of claim 7 further comprising a guard removably attached to the tubular inner sleeve at its distal end.

9. The splint of claim 8 wherein the guard comprises a tip end configured to receive a tip of a finger and a guard spine attached proximal to the tip end wherein the guard spine comprises a plurality of spine protrusions each configured to removably attach to one of the plurality of holes defined by inner sleeve.

10. The splint of claim 7 wherein the degree of taper is equal to or between 2 degrees and 4 degrees.

11. The splint of claim 1 wherein the inner diameter of the tubular inner sleeve tapers from a larger proximal end to a smaller distal end and wherein the inner diameter of the open tubular outer frame tapers from a larger proximal end to a smaller distal end.

12. The splint of claim 11 wherein the degree of taper is equal to or between 2 degrees and 4 degrees.

13. The splint of claim 2 further comprising a guard removably attached to the tubular inner sleeve at its distal end.

14. The splint of claim 13 wherein the guard comprises a tip end configured to receive a tip of a finger and a guard spine attached proximal to the tip end wherein the guard spine comprises a plurality of spine protrusions each configured to removably attach to one of the plurality of holes defined by inner sleeve.

15. The splint of claim 2 wherein the inner sleeve surface defines a plurality of longitudinal ridges.

16. The splint of claim 1 wherein the inner sleeve surface defines a plurality of longitudinal ridges.

17. A splint comprising:
   a) a flexible tubular inner sleeve having a proximal end and a distal end, the inner sleeve comprising:
      i) an outer sleeve surface defining a channel that surrounds a flex region, wherein the flex region is configured to cooperate with a bodily joint;
      ii) an inner sleeve surface;
      iii) a plurality of openings extending from the outer sleeve surface to the inner sleeve surface; and
      iv) a plurality of ridges extending longitudinally along the inner sleeve surface; and
   b) a semi-rigid and resilient open tubular outer frame having a proximal end and a distal end, the outer frame defining an opening wherein the outer frame fits in the channel of the inner sleeve and wherein the frame opening cooperates with the flex region of the inner sleeve when the outer frame is positioned in the inner sleeve channel, the outer frame comprising:
      i) a first ring section having a first end and second end;
      ii) a second ring section having a first end and a second end, wherein the second ring section is offset from the first ring section;
      iii) a first spine section connecting the first end of the first ring section to the first end of the second ring section; and
      iv) a second spine section connecting the second end of the first ring section to the second end of the second ring section, wherein the second spine section is offset from the first spine section and the connected first ring section, first spine section, second ring section, and second spine section define the perimeter of the frame opening of the outer frame.

18. The splint of claim 17 wherein the inner sleeve further defines a slot extending from its outer sleeve surface to its inner sleeve surface.

19. The splint of claim 18 wherein the inner diameter of the inner sleeve at its proximal end is larger than the inner diameter of the inner sleeve at its distal end and wherein the inner diameter tapers from the larger proximal end to the smaller distal.

20. The splint of claim 19 further comprising a guard removably attached to the tubular inner sleeve at its distal end wherein the guard comprises a tip end configured to receive a tip of a finger and a guard spine attached proximal to the tip end wherein the guard spine comprises a plurality of spine protrusions each configured to removably attach to one of the plurality of holes defined by inner sleeve.

\* \* \* \* \*